United States Patent [19]
Morita

[11] Patent Number: 5,730,753
[45] Date of Patent: Mar. 24, 1998

[54] ASSEMBLY FOR ADJUSTING PRICKING DEPTH OF LANCET

[75] Inventor: Susumu Morita, Nishinomiya, Japan

[73] Assignee: APLS Co., Ltd., Okayama, Japan

[21] Appl. No.: 809,521

[22] PCT Filed: Jul. 25, 1996

[86] PCT No.: PCT/JP96/02085

§ 371 Date: Jun. 5, 1997

§ 102(e) Date: Jun. 5, 1997

[87] PCT Pub. No.: WO97/04707

PCT Pub. Date: Feb. 13, 1997

[30] Foreign Application Priority Data

Jul. 28, 1995 [JP] Japan ................... 7-192987

[51] Int. Cl.[6] .................................. A61B 17/32
[52] U.S. Cl. ................. 606/181; 606/182; 128/770
[58] Field of Search ................... 606/181, 182; 128/770

[56] References Cited

U.S. PATENT DOCUMENTS

| | | | |
|---|---|---|---|
| 3,030,959 | 4/1962 | Grünert | 128/329 |
| 3,358,689 | 12/1967 | Higgins | 128/329 |
| 4,375,815 | 3/1983 | Burns | 128/314 |
| 4,379,456 | 4/1983 | Cornell et al. | 128/314 |
| 4,388,925 | 6/1983 | Burns | 128/314 |
| 4,414,975 | 11/1983 | Ryder et al. | 128/314 |
| 4,416,279 | 11/1983 | Lindner et al. | 128/314 |
| 4,442,836 | 4/1984 | Meinecke et al. | 128/314 |
| 4,449,529 | 5/1984 | Burns | 128/314 |
| 4,452,243 | 6/1984 | Leopoldi et al. | 128/314 |
| 4,462,405 | 7/1984 | Ehrlich | 128/329 R |
| 4,469,110 | 9/1984 | Slama | 128/770 |
| 4,503,856 | 3/1985 | Cornell et al. | 128/314 |
| 4,514,609 | 4/1985 | Fricke et al. | 200/159 A |
| 4,527,561 | 7/1985 | Burns | 128/314 |
| 4,535,769 | 8/1985 | Burns | 128/314 |
| 4,539,988 | 9/1985 | Shirley et al. | 128/314 |
| 4,545,376 | 10/1985 | Beiter | 128/314 |
| 4,553,541 | 11/1985 | Burns | 128/314 |
| 4,577,630 | 3/1986 | Nitzsche et al. | 128/314 |
| 4,580,564 | 4/1986 | Andersen | 128/314 |
| 4,580,565 | 4/1986 | Cornell et al. | 128/314 |
| 4,610,667 | 9/1986 | Pedicano et al. | 604/192 |
| 4,616,649 | 10/1986 | Burns | 128/314 |
| 4,624,253 | 11/1986 | Burns | 128/314 |
| 4,648,408 | 3/1987 | Hutcheson et al. | 128/770 |
| 4,653,513 | 3/1987 | Dombrowski | 128/765 |
| 4,658,821 | 4/1987 | Chiodo et al. | 128/314 |

(List continued on next page.)

FOREIGN PATENT DOCUMENTS

| | | |
|---|---|---|
| 0933 1992 | 10/1992 | Denmark . |
| 0 403 8723 | 12/1990 | European Pat. Off. . |
| 0 589 186 | 3/1994 | European Pat. Off. . |
| 0 613 656 | 9/1994 | European Pat. Off. . |
| 0 633 004 | 1/1995 | European Pat. Off. . |
| 92 05 278.9 | 8/1992 | Germany . |

*Primary Examiner*—Michael Buiz
*Assistant Examiner*—David O. Reip
*Attorney, Agent, or Firm*—Leydig, Voit & Mayer, Ltd.

[57] ABSTRACT

There is provided an assembly capable of more simply adjusting a pricking depth of a pricking element and being mounted onto an injector.

The assembly comprises a cap element enabled to be mounted onto the injector and having a stop means constructed such that an end of a lancet from which the pricking element protrudes abuts against the stop means after ejecting the lancet so that movement of the lancet is stopped while the pricking element is exposed outside out of the cap element, a cover element through which the pricking element exposed outside extends and which has an opening against which an object to be pieced is placed, and a adjusting element which engages the cap element and the cover element between these elements, and a distance between the stop means and the opening along a direction of the lancet ejection is changed by rotation of the adjusting element around an axis of the direction of the lancet ejection.

20 Claims, 5 Drawing Sheets

U.S. PATENT DOCUMENTS

| | | | |
|---|---|---|---|
| 4,676,244 | 6/1987 | Enstrom | 128/314 |
| 4,677,979 | 7/1987 | Burns | 128/314 |
| 4,712,548 | 12/1987 | Enstrom | 128/314 |
| 4,715,374 | 12/1987 | Maggio | 128/314 |
| 4,735,203 | 4/1988 | Ryder et al. | 128/314 |
| 4,738,261 | 4/1988 | Enstrom | 128/314 |
| 4,794,926 | 1/1989 | Munsch et al. | 128/314 |
| 4,817,603 | 4/1989 | Turner et al. | 128/329 R |
| 4,844,095 | 7/1989 | Chiodo et al. | 128/314 |
| 4,856,515 | 8/1989 | Turner et al. | 128/315 |
| 4,858,607 | 8/1989 | Jordan et al. | 128/314 |
| 4,869,249 | 9/1989 | Crossman et al. | 128/314 |
| 4,889,117 | 12/1989 | Stevens | 606/181 |
| 4,892,097 | 1/1990 | Ranalletta et al. | 606/182 |
| 4,895,147 | 1/1990 | Bodicky et al. | 606/182 |
| 4,924,879 | 5/1990 | O'Brien | 128/770 |
| 4,976,724 | 12/1990 | Nieto et al. | 606/182 |
| 4,990,154 | 2/1991 | Brown et al. | 606/182 |
| 4,994,068 | 2/1991 | Hufnagle | 606/181 |
| 4,995,402 | 2/1991 | Smith et al. | 128/771 |
| 5,026,388 | 6/1991 | Ingalz | 606/182 |
| 5,100,427 | 3/1992 | Crossman et al. | 606/182 |
| 5,105,823 | 4/1992 | Blum | 128/754 |
| 5,133,730 | 7/1992 | Biro et al. | 606/182 |
| 5,147,375 | 9/1992 | Sullivan et al. | 606/182 |
| 5,207,699 | 5/1993 | Coe | 606/182 |
| 5,318,584 | 6/1994 | Lange et al. | 606/182 |
| 5,324,303 | 6/1994 | Strong et al. | 606/181 |
| 5,356,420 | 10/1994 | Czernecki et al. | 606/182 |
| 5,366,469 | 11/1994 | Steg et al. | 606/182 |
| 5,366,470 | 11/1994 | Ramel | 606/183 |
| 5,397,334 | 3/1995 | Schenk et al. | 606/182 |
| 5,439,473 | 8/1995 | Jorgensen | 606/182 |
| 5,464,418 | 11/1995 | Schraga | 606/182 |
| 5,487,748 | 1/1996 | Marshall et al. | 606/182 |
| 5,554,166 | 9/1996 | Lange et al. | 606/182 |

ASSEMBLY FOR ADJUSTING PRICKING DEPTH OF LANCET

FIELD OF INVENTION

The present invention relates to an assembly which is mounted onto an injector (or a projector) which ejects (or projects) a lancet (a needle for blood collection) from which a pricking element protrudes, and the assembly adjusts a pricking depth of the pricking element into an object to be pricked.

BACKGROUND ART

Diabetes is classified into insulin dependent diabetes mellitus (IDDM) and non-insulin dependent diabetes mellitus(NIDDM). It is said to be desirable that a patient of IDDM has to measure his/her blood sugar concentration several times a day, and even a patient of NIDDM has to measure his/her blood sugar concentration several times a week.

Search carried out by WHO shows results that a remainder of life of a diabetes patient who self-controls his/her blood sugar concentration to surely keep at a given level while his/her blood sugar concentration is frequently measured and referred to is clearly longer than that of a patient who does not control so.

In order to measure a blood sugar concentration using commercially available test paper for blood sugar concentration measurement, blood has to be collected in an amount between several microliters and 20 µl depending on a performance of the paper. For such collection, a lancet and an injector which ejects the lancet are used, and blood is usually collected from a finger tip.

A commercially available lancet has a needle as a pricking element of which diameter is 0.8 mm (20 gauge), 0.65 mm (23 gauge), 0.5 mm (25 gauge) or 0.4 mm (28 gauge), and its pricking depth into a skin is in the range between about 2.3 mm and 3 mm.

The diabetes patients range over the infant, the adult and the old or the male and the female, and over various human races, on which a skin thickness of the finger tip from which the blood is collected depends. However, as the lancet used for the blood collection, those having the above mentioned pricking elements are often used. By the way, a manufacturer who produces an apparatus for blood sugar concentration measurement usually sells, in addition to the test paper, a lancet and an injector which ejects (or projects) the lancet.

In order to adapt to different skin thicknesses of a patient or to change an amount of blood to be collected, there have been only provided two types of cap elements which are so constructed that they are mounted onto an end of the conventional injector: one of which has a thicker end surface (or thick wall) having an opening (for shallower pricking); and the other of which has a thinner end surface (or thin wall) having an opening (for deeper pricking). Then, the pricking depth can be changed by replacing the cap with the other. Thus, the depth may be very roughly changed, for example 0.4 mm or 0.7 mm.

Therefore, the following have occurred: The infants having a thin skin has to be pricked through a longer depth than necessary everyday so that their fingers have been considerably damaged. On the other hand, the adult male who has a relatively thick skin cannot collect an effective amount of blood.

In order to solve the above problems, Boehringer Mannheim GmbH (Germany) has sold "Softclix (registered trade mark)" as a blood collection assembly since 1993 which can adjust the pricking depth of the pricking element of the lancet step-wise using a single cap element.

The assembly can adjust the pricking depth of the pricking element of the lancet in multi steps (six steps) by rotating the cap element which is mounted onto an end of an injector body. An adjustable span in six steps total is about 1.2 mm and thus one step can change the depth by 0.2 mm.

Known assemblies such as "Softclix" have good mechanisms for locking a spring as an elastic element which ejects the lancet and for releasing the locked state so as to eject the lancet. However, those mechanisms are complicated and thus the number of parts becomes large, so that the known assemblies are expensive compared with injectors which have been sold before.

As to "Softclix", no stop means for stopping the ejected lancet is provided on the cap element which is mounted onto the injector end. Movements (forward and backward movement) of the lancet through the injector (i.e. an injector body including an end cap attached thereto) are all controlled by mechanisms in the injector body, and thus a distance of the forward movement or the backward movement of the lancet (i.e. a movement stroke of the lancet) is always constant.

Using the above mechanisms, the pricking depth of the lancet is adjusted by rotating the cover element which is mounted onto an end of the cap element attached to the injector so that a distance from an opening of an end surface of the cover element to a needle tip (before the ejection of the lancet) is made shorter for achieving to a longer pricking depth or longer for achieving to a shorter pricking depth. Since the movement stroke of the lancet has to be constant, the cap element cannot be used for any other commercially available injector in place of "Softclix." In addition, the lancet itself to be used has to have in a specific configuration and particular a predetermined total length within a strict tolerance, so that it is necessary to use an exclusive lancet and an exclusive end cap and injector, otherwise no advantage is conveniently obtained from adjusting the pricking depth. With respect to this view point, other injectors rather than "Softclix" generally have an advantage that they can use any of the commercially available several types of the lancets without replacing the cap element.

The problems of the prior art as described above are summarized as follows: The prior art injectors rather than Softclix cannot adjust the pricking depth of the lancet without replacing the end cap. However, they have the advantage that a single injector of them can use the several types of the commercially available lancets.

With respect to "Softclix", a single injector (i.e. a combination of the injector body and the cap element) advantageously has a function to adjust the pricking depth of the lancet. However, the exclusive injector and cap element and the exclusive lancet have to be used. Thus, it is very convenient to the diabetes patients if an assembly is provided which is attached to the commercially available injector body, with which the commercially available lancet can be used and which enable the pricking depth of the lancet to be adjusted with a single cap element.

DISCLOSURE OF INVENTION

It is an object of the present invention to provide an assembly which overcomes the problems of the prior art related to the adjustment of the pricking depth as described above and which is combined with the commercially available blood collecting device and enables the pricking depth of the pricking element to be adjusted more conveniently and surely.

In the first aspect, the present invention provides an assembly which is attached to an injector which ejects a lancet having a pricking element protruding therefrom and which adjusts a pricking depth of the pricking element into an object to be pricked, the assembly consisting substantially of

- a cap element which is enabled to be attached to the injector and which has a stop means which stops movement of the lancet (while the pricking element is exposed outside the cap element after the lancet is ejected) by abutment of an end of the lancet from which the pricking element protrudes against the stop means,
- a cover element through which the pricking element exposed outside extends and which has an opening against which the object to be pricked is placed, and
- an adjusting element which engages the cap element and the cover element between these elements,
- a distance between the stop means and the opening along a direction of the lancet ejection being variable by rotation of the adjusting element around a direction of the lancet ejection as a pivot. In the present assembly, the cover element is located outside the cap element.

In the present assembly, the cover element, the adjusting element and the cap element are positioned substantially coaxially, and the cover element and the adjusting element are able to rotate together around the direction of the lancet ejection as an axis. Further, the adjusting element and the cap element are so constructed that they are able to achieve an engagement relationship by means of a screw mechanism.

In addition, the cap element includes a cap element thread portion on the outside of an end portion thereof. In a preferable embodiment, the cover element may have a protruding portion on the inside thereof. The adjusting element may have an adjusting element thread portion on the inside thereof which is engaged with the cap element thread portion, and the adjusting element may have a recess portion on the outside thereof which is engaged with the protruding portion of the cover element in the said preferable embodiment. Further, the cap element may have a stop portion which limits the rotation of the adjusting element by abutment of a protruding portion of the adjusting means against the stop portion.

The adjusting element preferably has a plurality of slits which extend from its end attached to the injector so that the adjusting element is divided into flap portions which are connected together at the other end of the adjusting element, whereby the flap portions are able to be elastically deformed while supported at the other end as a base, and particularly they can open outward. However, once the cover element has been engaged with the adjusting element, the elastic deformation of the adjusting element is limited by the cover element.

In the second aspect, the present invention provides a blood collection device which comprises the assembly of adjusting the pricking depth of the pricking element (which is described above and will be described in detail below) and an injector.

In the third aspect, the present invention provides each of the elements of the assembly of adjusting the pricking depth of the pricking element which is described above and will be described in detail below, namely the cap element, the adjusting element and the cover element.

In the drawings, numeral 1 indicates an assembly of adjusting a pricking depth, numeral 3 does a cap element, numeral 5 does an adjusting element, numeral 7 does a cover element, numeral 9 does an end portion, numeral 11 does an end portion, numeral 13 does a stop means, numeral 15 does an opening, numeral 17 does a cap element thread portion, numeral 19 does a slit, numeral 21 does a flap portion, numeral 23 does a tab portion, numeral 25 does a protruding portion, numeral 29 does a recess portion, numeral 31 does an opening, numeral 33 does an opening against which an object to be pricked is placed, numeral 35 does an end surface, numeral 37 does a peripheral step portion, numeral 39 does a recess portion for clicking, numeral 41 does a recess portion, numeral 43 does a stop portion, numeral 45 does an annular ring portion, numeral 47 does a thread groove, numeral 51 does a protruding portion, numeral 53 does a thread portion thread portion, numeral 55 does a recess portion, numeral 57 does a protruding portion for clicking, numerals 61 and 63 do wall portions, numeral 65 does a protruding portion, numeral 71 does a cavity, numeral 73 does a pricking element, numeral 75 does a lancet, numeral 77 does an lancet end, numeral 81 does a rear end of the cap element, and numeral 83 does an injector (or an injector body).

DETAILED DESCRIPTION OF INVENTION

The assembly of adjusting the pricking depth of the pricking element of the present invention will be hereinafter explained in detail, which description will be also applicable to the blood collection device as well as the cap element, the adjusting element and the cover element according to the present invention provided that the description is appropriate to them.

In the present invention, the pricking element is an element having a sharp tip or edge portion which injures an object to be injured, namely an object to be pricked, for example a skin such as a finger tip, and concretely exemplified by an element in the form of a needle or a blade. It is noted that "pricking" means that the pricking element injures the object to be injured to an extent that the object bleeds. The lancet having such a pricking element is an element having the pricking element used for conveniently collect blood as described in the background art description. The lancet is so constructed that it is projected by the injector toward the object to be pricked and then the pricking element injures the object to be pricked.

The injector has a mechanism which stores a force by keeping an elastic element such as a spring in a compressed state, and then ejects the lancet toward the object to be pricked as a blood collection site by releasing the compression state of the elastic element and using a force of the element to recover toward its original state.

The pricking element and the lancet having the element as well as the injector as described above are well-known elements or devices and no additional detail description would not be necessary. Concretely, the lancet which can be used in combination with the present invention is commercially available as Ames Lancet (trade name of Bayer), Monolet (trade name of Sherwood) or Lancets (trade name of Lifescan), and the injector which can be used in combination with the present invention is commercially available as Glucolet (trade name of Bayer) and Penlet II (trade name of Lifescan).

The pricking depth means an extent of a depth by which the pricking element penetrates into the object to be pricked. The pricking depth corresponds to a length of the pricking element which is exposed out of the opening of the cover element against which the object is placed. The present invention enables the length to be changed as required, namely, adjusted. In principle, the adjustment of the depth is related to adjustment of a bleeding amount from the object to be pricked.

The assembly of adjusting the pricking depth according to the present invention comprises the cap element, the cover element and the adjusting element, and is so constructed that a relative positional relationship between the cap element and the cover element is changed along the direction of the lancet ejection by rotative movement of the adjusting element around an axis along the direction of the lancet ejection.

As to the assembly according to the present invention, any element is preferably made of a plastic material. Considering conveniences in assembling the elements and using the assembly, it is particularly preferably that the adjusting element and other element adjacent thereto are made of different plastic materials from each other, but it is of course possible that they are made of the same material. Considering that the adjusting element preferably has portions which can be elastically deformed repeatedly and has flex resistance as described below, the adjusting element is preferably made of a so-called engineering plastic material such as a polyacetal, a polybutylene terephthalate (PBT) or a polyamide (such as Nylon 6, Nylon 6—6). On the other hand, the material for the cap element or the cover element does not have to have so large elasticity or flex resistance as the adjusting element and it is sufficient that the material have general stiffness. Thus, a general purpose plastic material is sufficient such as an ABS resin, an HI (high impact) polystyrene, a polypropylene and a polyethylene. Of course, the engineering plastic material as described above may be possible. The material of any element preferably has some resistance against an agent which is used for disinfection or washing of the element.

The cap element of the assembly of the present invention comprises an injector connecting means at its one end which is engaged with the injector (or an injector body), and a stop means which prevents the lancet from further moving along the lancet ejection direction from a predetermined position after the lancet ejection (for example, the stop means is an end surface). The injector connecting means is for engagement of the injector with the cap element and there is no specific limitation on the means provided that the engagement is achieved. Usually, the connecting means is positioned at or near the end of the cap element which is positioned to be nearer to the injector, and the injector has a means which is engaged with the connecting means of the cap element. Concretely, such a means may be a recess portion (when a commercially available injector has a protrusion portion) or a protrusion portion (when a commercially available injector has a recess portion) so that the cap element can be snap-fitted onto the injector. Alternatively, the injector and the cap element are engaged with each other through a screw mechanism.

As described above, the stop means of the cap element may be the end face of the cap element which is opposite to the end having the injector connecting means. The end surface preferably has an opening in its center. A shape of the opening may be selected depending on a shape of a cross-section of the pricking element which passes through the opening. The opening may be circular when the pricking element is a needle, and the opening may be rectangular or an elliptic when the pricking element is a blade.

Upon the collection of blood, the elastic element of the injector extends beyond its original free state with release of the stored energy so that the lancet which behaves together with the elastic element is ejected forward and the pricking element passes through the opening of the cap element, and then the end of the lancet having the pricking element strikes the stop means, whereby the movement of the lancet is stopped instantaneously and a kinetic energy of the lancet is absorbed by the stop means. Thereafter, the elastic member of the injector returns to its original free state due to its spring back (i.e. its recovery behavior to its original state). The injector is usually so constructed (for example by properly adjusting the elastic element) that a tip of the pricking element goes back from the opening of the stop means into a position that the tip is retracted inside of the cap element.

At the moment when the movement of the lancet is stopped by the stop means, the pricking element of the lancet is in such a position that the pricking element has passed the opening at the stop means and been exposed to the outside of the cap element. In such an exposed position, the pricking element has passed also through the opening of the cover element as described below so that it has been exposed to the outside of the cover element, which allows the pricking element to prick the object to be pricked which is abutted against the opening.

In the assembly of adjusting the pricking depth according to the present invention, the cover element and the adjusting element are so constructed that they are rotated together when they are assembled. That is, rotation of the cover element around a direction of the lancet ejection as an axis rotates the adjusting element similarly, so that the adjusting element rotates by substantially the same degrees of an angle (central angle) toward the same rotative direction as the cover element. For example, the cover element has a protruding portion on its inside and the adjusting element has a recess portion on its outside with which the protruding portion is engaged. The engagement of the protruding portion with the recess portion allows the both element to behave together around a direction of the lancet ejection by the rotative action.

The cap element includes a cap element thread portion on its outside of or near the end portion thereof which includes the stop means, and the adjusting element has an adjusting element thread portion on its inside. These thread portions are in a relationship that they are engaged with each other based on a screw mechanism. In the present specification, the relationship being "engaged with each other based on a screw mechanism" with respect to the cap element thread portion and the adjusting element thread portion means that a thread portion of one element is complementally fitted into a thread groove of the other element so that when one element is rotated relative to the other element around the lancet ejection direction as an axis, one element moves forward or backward relative to the other element along the lancet ejection direction.

Such a relationship is concretely formed by that the both elements have threads which constitute the so-called bolt-and-nut relationship, in which the thread of one element is preferably discontinuous. In the present specification, the discontinuous thread means that the tread may be partially absent on the way along its spiral, in which partially present tread portions necessarily on the spiral having the same pitch. In a more preferable embodiment, the partially present thread portions are provided on the inside of the adjusting element. The partially present thread portions may be such that most of their original basic thread are eliminated. For example, the partially present thread portion may be of a point or a projection (or protrusion) (in the form having for example a circular or rectangular cross section) of which length along the spiral direction may be almost the same as the pitch of the thread spiral. Merely provision of at least one such point or projection, preferably at least two such points or projections symmetrically around the rotation axis of the thread, and more preferably at least three or four such points or projections symmetrically around the rotation axis of the thread allows them to function as a thread. This is based on that the assembly according to the present invention does not require so large an engagement force (fastening force) between the cap element and the adjusting element.

The cap element of the assembly according to the present invention has a step portion along its whole periphery near the cap element thread portion, for example adjacent thereto. The step portion includes a plurality of recess portions into which a protruding portion provided on the adjusting element is fitted so that clicking may be carried out as described below. The protruding portion is provided at a position which is remote a little from the end of the adjusting element. This step portion also functions as a wall which defines a recess portion as described below.

The cap element according to the present invention has at least one partial recess portion along a peripheral direction of the cap element near, for example adjacent to the step portion, and the adjusting element has a protruding portion on its end (which is also referred to as a "tab portion") and a shape of the protruding portion is adapted to being placed into the recess portion. A length along the lancet ejection direction of the recess portion is substantially at least a maximum variable pricking depth range (namely, a difference of the maximum distance from the minimum distance between the stop means of the cap element and the opening of the cover element against which the object to be pricked is placed)+a length of the protruding portion to be placed into along the lancet ejection direction. A peripheral length of the recess portion (thus, a length of the recess portion perpendicular to the lancet ejection direction) is at least equal to a peripheral length which corresponds to an angle achieving necessary rotation of the adjusting element so as to obtain the maximum variable range of the pricking depth (namely, an arc length corresponding to an angle of the necessary rotation)+a peripheral length of the protruding portion. More preferably, two or three such recess portions are provided on the cap element around the rotation axis symmetrically so that each recess portion is separated by a stop portion from each other.

A level of this stop portion is higher than that of the step portion (namely, an outer surface of the stop portion extends beyond an outer surface of the step portion). Thus, in the case where the cap element and the adjusting element are rotated to approach to each other using the screw mechanism (of course, the cover element has not yet been positioned on the cap element), the levels of the step portion and the stop portion are such that the end of the adjusting element or the protruding portion provided thereon can easily ride up the step portion due to the elasticity of the adjusting element, but cannot ride over the stop portion when the rotation is further continued. Thus, the rotation is once prevented when the protruding portion or the end of the adjusting element abuts against the stop portion.

After the rotation is thus once stopped, when a little larger force is applied along the rotation direction, the adjusting element is deformed to open a little due to its elasticity so that the protruding portion or the end can ride up and over the stop portion and then fall (or be placed) into the recess portion which is adjacent to the stop portion. Once the protruding portion has fallen into the recess portion, the adjusting element returns to its original construction (namely closes), the protruding portion is such that it cannot get out of the recess portion by riding up and over a wall which defines the recess portion with application of a rotative force provided that a larger force is intentionally applied so as to open the adjusting element. Thus, the protruding portion is movable only within the recess portion.

The placement of the protruding portion into the recess portion by means of the rotation of the cap element and the adjusting element has been explained above. Such placement (namely, positioning of the protruding portion into the recess portion) may be also achieved by means of bringing the adjusting element close to the cap element coaxially along an axial direction and putting the adjusting element on the cap element. This is because the adjusting element opens elastically so that riding over the thread of the screw portion and the step portion of the cap element becomes possible. In addition, this manner may be combined with the manner using the rotation. For example, there is a manner in which bringing close to each other is carried out halfway and then the rotation manner is carried out, or vice versa. As to the elasticity of the adjusting element will be explained below.

The protruding portion(s) of which number corresponds to the number of the recess portion(s) and which are provided on the inside at or near the injector side end of the adjusting element are such that they fall into the recess portion(s) as described above. After the protruding portion has been placed into the recess portion, the cover element is positioned onto the adjusting element so that the cover element prevents the deformation of the adjusting element so as to interferes outward movement of the tab portion having the protruding portion. Thus, after the provision of the cover element onto the adjusting element, the placement of the protruding portion of the adjusting element into the recess portion of the cap element is completely maintained and only the partial axial rotation of the adjusting element is possible around the cap element.

The adjusting element of the present invention is made of the elastically deformable material, and is of a cylinder form as a whole. It has a plurality of slits extending along the lancet ejection direction from the end thereof near the injector, and those slits divide the cylindrical side surface of the element into a plurality of peripheral flap portions. These flap portions are connected together at the other end of the adjusting element through an annular ring portion. Thus, the peripheral flap portions can be opened when a some force is applied thereto as described above, and substantially return to their original shape when the force is removed. (Of course, when a force is applied in a reverse direction, they deform and when the force is removed, they return.) The property as just described above is referred to as elasticity, which makes the incorporation of the adjusting element onto the cap element easy as described above. Such elasticity is obtained by the material used for the adjusting element and the slits.

Thus, a size relationship between the adjusting element and the cap element on which the adjusting element is put does not have to achieve a tight engagement only with the both, and it is rather preferable that there is a small space (or clearance) between them so as to make the incorporation of the adjusting element onto the cap element easier. A situation of the small space is changed to a situation of substantially absence of the space when the cover element is put on the adjusting element so that the inside of the cover element presses at least a portion of the adjusting element (for example, a protruding portion) and the pressed adjusting element in turn presses the cap element inwardly. As a result, the rotation of the cap element relative to the adjusting element is possible while the cap element, the adjusting element and the cover element are engaged tightly.

The pricking depth of the assembly of the present invention can be adjusted continuously by changing a rotation angle of the adjusting element relative to the cap element. However, the assembly is conveniently so constructed that it is clicked to change the pricking depth by a predetermined pricking depth interval. In order to click so, the cap element may have at least one recess portion on the step portion and the adjusting element may have a protruding near the end of the element as the tab portion of the flap portion which protrusion is adapted to being fitted in the recess portion.

The adjusting element has at least one recess portion on its outside which allows the element to be engaged together and rotate together with the cover element. The recess portion is provided adjacent to the end which is remote from the injector side and so shaped and sized that the recess portion is engaged with a protruding portion provided onto the inside of the cover element. The adjusting element and the cover element are preferably such that they are engaged with each other by means of snap-fitting.

The cover element is in the form of a cylinder having both ends, and one end near the injector is fully opened so that the adjusting elements and the underlying cap element pass through such an opening. The other end has an end surface against which the object to be pricked is placed, and the end surface has an opening in its center through which the pricking element of the ejected lancet passes. Immediately after pricking the object, the pricking element is retracted inside. A shape of the opening is similar to that of the opening of the cap element.

A distance between the end of the cap element through which the pricking element passes and the end of the cover element (against which the object is to be placed) is shorter than a protruding length of the pricking element from the lancet end, and considering that such a protruding length is not so long (for example about 3.2 mm), the distance is preferably about 2.4 mm at the maximum and about 1.4 mm at the minimum. Thus, in a preferable embodiment, the end of the cap element is spaced from the end surface of the cover element having the opening for the pricking element through the annular ring portion of the adjusting element by a distance which provides the shortest pricking depth (thus, the distance is the longest), or a distance which provides the longest pricking depth (thus, the distance is the shortest).

In order to assemble the assembly according to the present invention, the adjusting element is put on the end portion of the cap element, and then these elements are relatively rotated in a direction so that the screw mechanism brings these element close to each other. After the rotation is once stopped when the end of the adjusting element abuts against the stop portion, a larger force is further applied to continue the rotation so that the end get over the stop portion, whereby the protruding portion provided onto the end of the adjusting element falls into the recess portion of the cap element. Alternatively, the cap element and the adjusting elements may be brought close to each other along the axial direction thereof so that the protruding portion falls into the recess portion. Thereafter, the cover element is pushed onto the adjusting element axially so as to fit the protruding portion of the cover element into the recess portion provided outside the adjusting element, whereby the assembly of adjusting the pricking depth according to the present invention is finally completed.

With the completed assembly, the pricking depth is adjusted by rotating the cover element relative to the cap element depending on a desired amount of blood to be collected. In order to facilitate this adjustment, either or both of the cover element and the cap element may be provided with a mark for identifying a rotation position of the cover element and the cap element, numerals which shows an adjusted pricking depth and so on.

The completed assembly is attached onto an injector (or an injector body) to which a lancet has been already placed. Such attachment is carried out using engagement means which are provided on the injector body and the cap element (for example, snap fitting is used for the attachment).

The injector bodies of commercially available injector have various shapes and sizes, and the means with which the cap element is attached to the injector body are different such as a screw means or a snap fitting means. In order that the assembly according to the present invention is adapted to those various injector bodies, the cap element is designed to adapt to the injector body, and the adjusting element and the cover element do not have to be changed. It is contemplated that when four types of the end caps are prepared which are adapted to the injector bodies of the commercially available typical injectors (Ames Glucolet (from Bayer), Penlet II (from Lifescan), Exact Tech (from Palco) and Home Diagnostic (from Dialet)), diabetes patients using the commercially available lancet can enjoy the merit of the adjustment of the pricking depth of the lancet.

In order to wash or disinfect the assembly, the cover element can be easily pulled out along the lancet ejection direction, and then the cap element on to which the adjusting element is attached and the cover element can be washed, respectively. Further, the adjusting element is reversely rotated with a large force or the flap portions are opened so that the end of the adjusting element can be out of the recess portion and then the adjusting element is rotated in an unfastening direction or is directly pulled out as it is, whereby the adjusting element is disengaged from the cap element. Thus, the assembly according to the present invention can be disassembled into each element separately, which can be washed and then assembled again.

As described above, the flap portions of the adjusting element are opened around the annular ring portion as the base (or axis) and return to their original forms upon assembling into the assembly or disassembling for washing, and thus the adjusting element is in particular preferably made of the material having the flex resistance (or fatigue resistance).

EMBODIMENT OF INVENTION

The assembly according to the present invention will be explained with reference to the accompanying drawings.

Figure 1:
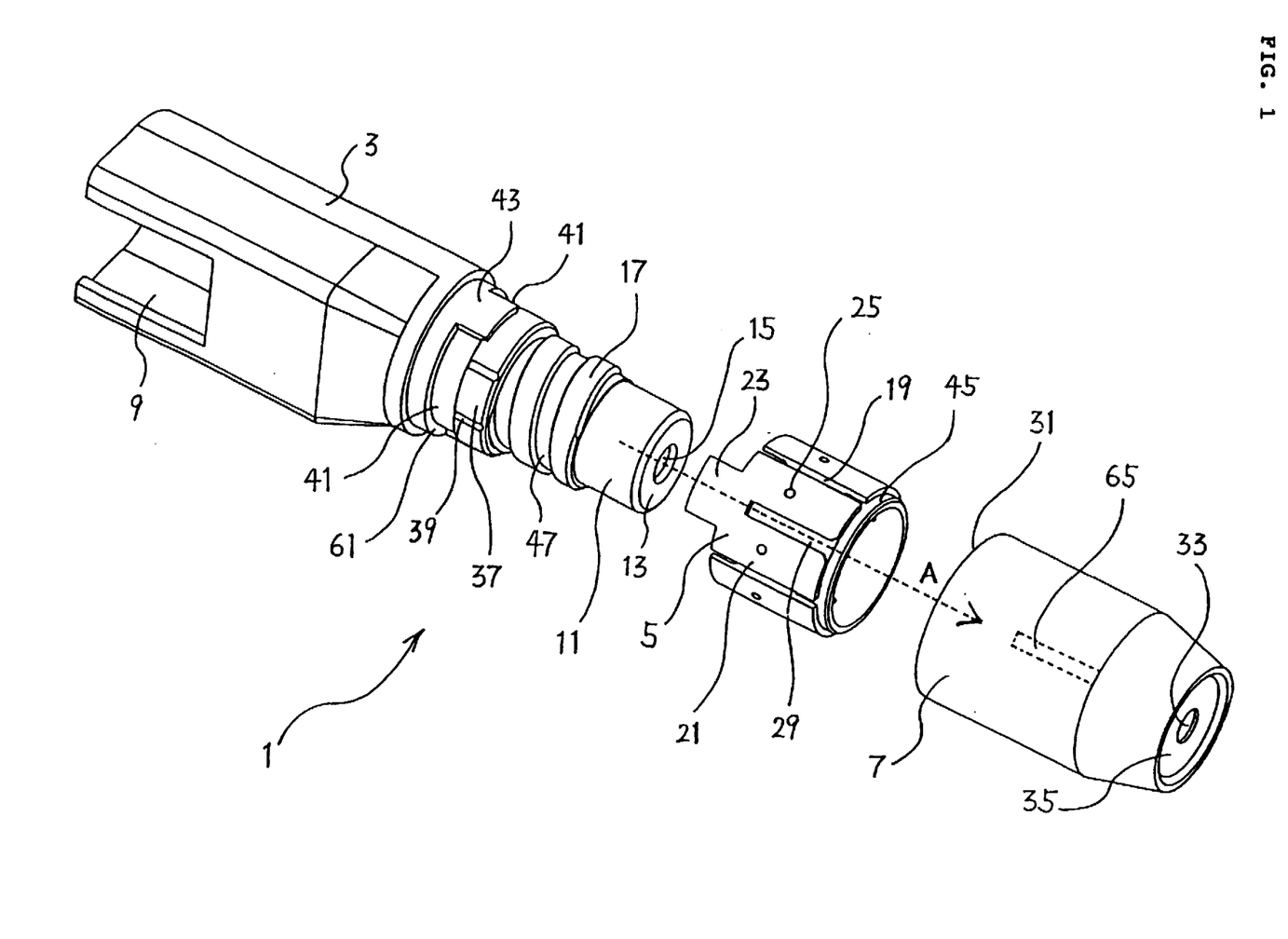
FIG. 1 schematically shows an exploded perspective view of the assembly of adjusting the pricking depth of the pricking element according to the present invention.
Figure 2:
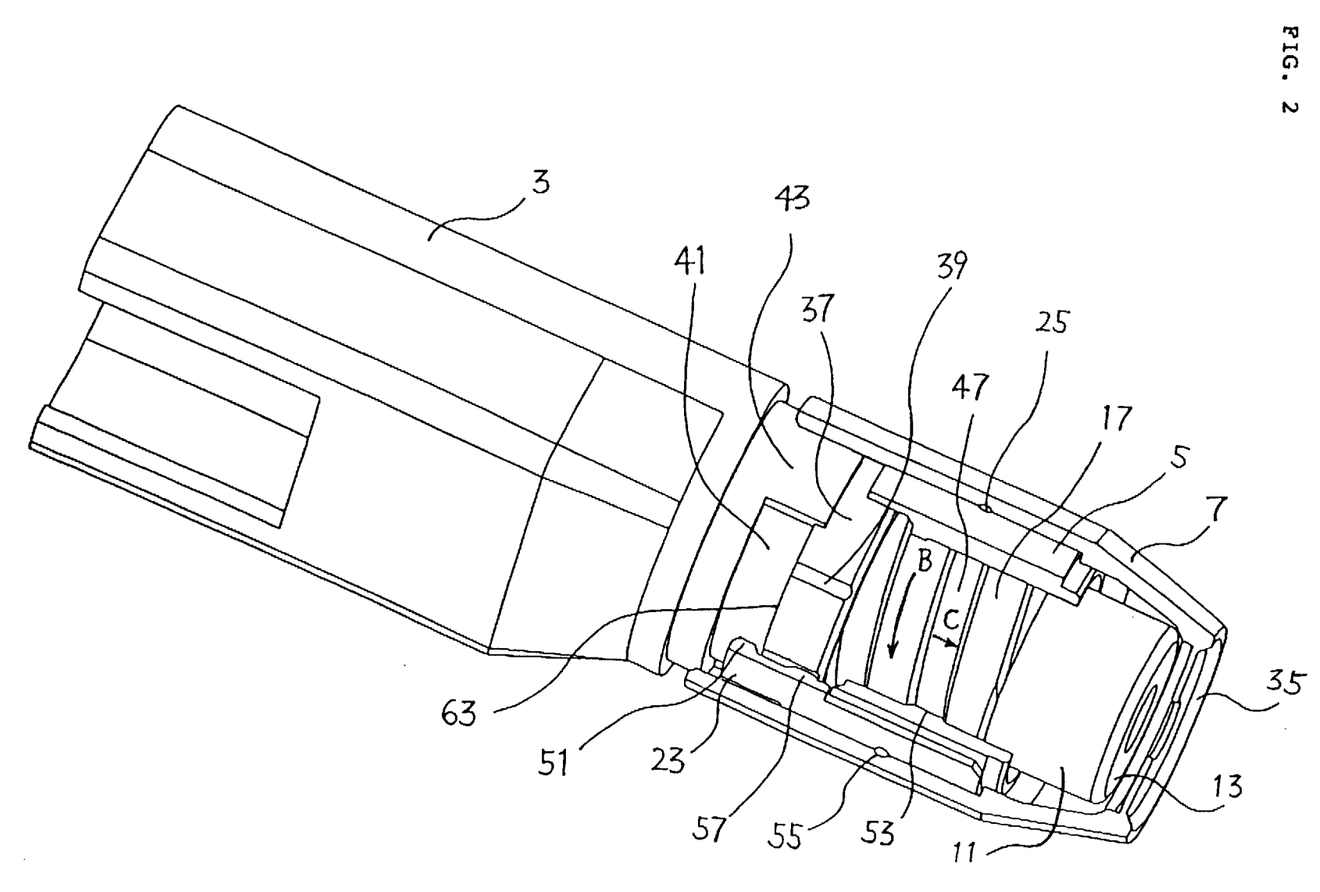
FIG. 2 schematically shows a partially cut away perspective view of the assembly of adjusting the pricking depth of the pricking element according to the present invention after assembling.

One example of preferable embodiments of the assembly of adjusting the pricking depth according to the present invention is shown in FIG. 1 in an exploded perspective view and in shown in FIG. 2 in a partially cutaway and assembled perspective view. As shown in the drawings, the assembly 1 is composed of the cap element 3, the adjusting element 5 and the cover element 7. The adjusting element 5 is put onto the end portion 11 of the cap element 3 and then rotated or pushed into as it is, and then the cover element 7 is pushed onto and fitted to the adjusting element 5, whereby the present assembly 1 according to the present invention is completed.

Although the end portion 11 of the cap element 3, the adjusting element 5 and the cover element 7 have some concave and convex surfaces, the assembly according to the present invention is generally in the form of a cylinder and preferably a cylinder partially containing tapered portions. The assembly has been formed by assembling those elements coaxially.

As to the cap element 3, its one end portion 9 is so constructed that an injector (not shown) is fitted into the end portion for engagement, and the adjusting element 5 is mounted onto other end portion 11. The other end portion 11 comprises a cylindrical portion having the stop means 13, the cap element thread portion 17, the step portions 37 and the recess portions 41. An end surface of the end portion 11 functions as the stop means 13 and has the opening 15 in its center portion.

Although not shown, an engagement means is provided onto the inside of the end portion 9 of the cap element 3, and the injector has an engagement means which is mated with the engagement means of the cap element.

The engagement of the cap element 3 with the injector may achieved in any suitable manner. For example, the cap element 3 is conveniently mounted onto or disengaged from the injector with snap-fitting or screw mechanism fastening. The embodiment shown in the drawings corresponds to the snap-fitting engagement, and a protruding portion (which cannot be seen) of the cap element 3 is such that it is engaged with a recess portion of the injector.

After a lancet has been ejected by the injector, it rapidly moves within the inside of the cap element 3 along a direction of the arrow A and a pricking element of the lancet passes through the opening 15 to expose out of the cap element 3. Thus, a tip of the pricking element passes through the opening 33 of the cover element 7 and is exposed outside of the cover element 7. On the other hand, an end portion of the lancet abuts against the inside of the end surface 13 so that kinetic energy that the lancet has is absorbed, immediately after which the lancet goes back toward the injector (i.e. a direction opposite to the arrow A) by an elastic member of the injector which tends to recover its original free state. That is, the lancet is retracted into the inside of the cap element 3 through the opening 15.

As to the cap element 3, the end portion 11 includes the thread portion 17, which may be such that ridge and groove portions are flat as shown or have U or V-shaped cross sections. The number of turns of the thread is not specifically limited, but a lead of the thread (a proceeding length of the thread with one turn) is selected so that preferably about half turn (or rotation), and more preferably about ⅛–⅘ turn achieves a whole variable pricking depth range (i.e. from the deepest pricking depth to the shallowest pricking depth). By such selection, a desired pricking depth is available without unnecessarily large number of rotations.

The cap element 3 has the peripheral step portion 37 which is adjacent to the thread portion 17, and the step portion includes at least one recess portion (for example groove) 39 for clicking. The recess portion has a shape and a size which allow the protruding portion 57 provided onto the adjusting element 5 (see FIG. 2) to fit into the recess portion 39 so as to achieve clicking. Thus, the adjusting element 5 and the cap element 3 are in an engagement state with clicking at a predetermined rotation position so that a user easily recognizes that a desired pricking depth has been set.

Further, the cap element 3 comprises at least two peripheral recess portions (concave portions) 41 adjacent to the step portions 37 into which recess portions the protruding portions 51 provided on the end portions 23 of the adjusting element 5 are placed respectively, whereby the adjusting element 5 is engaged with but axially rotatable around the cap element 3. Each of those plural recess portions 41 has a predetermined peripheral length and a predetermined axial length (or width), and they are separated by the stop portion 43 from each other. Therefore, the recess portions 41 and the stop portions 43 are arranged alternatively around the cap element 3 symmetrically and regularly. Thus, the protruding portion 51 placed into the recess portion 41 can move along the same direction as that of the thread portion, but the movement within the portion 41 is limited along the peripheral direction since the protruding portion 51 abuts against the stop portion 43 at an end of the recess portion 41. As to movement along an axial direction, the adjusting element 5 moves axially relative to the cap element 3 by the rotation thereof, and the width of the recess portion 41 is such that it does not prevent the axial relative movement. That is, the protruding portion 51 has to be moved axially in the recess portion 41 by a distance by which the adjusting element 5 axially moves relative to the cap element 3.

A peripheral length of the recess portion 41 is such that the adjusting element 5 can be rotated as desired. That is, the length is one which is required for the thread portion 17 to follow so as to achieve a desired variable pricking depth range. Also, an axial length of the recess portion 41 is one which allows the desired rotation.

The adjusting element 5 is generally in the form of a cylinder as a whole, and so constructed that it receives the end portion 11 of the cap element 3 except the vicinity of the end surface 13 in the inside thereof. The adjusting element 5 comprises a plurality of the slits 19 which extend longitudinally from an end of the element 5 which is near the injector when the assembly is assembled. These slits divide a cylindrical side surface of the adjusting element into a plurality of the peripheral flap portions 21, which are connected together at the other end through the annular ring portion 45. The flap portions 21 can be opened outward elastically at the annular ring portion 45 as a base.

At least one of the peripheral flap portion 21 comprises the tab portion 23 which has the protruding portion 51 on its inside end. The protruding portion 51 falls into the recess portion 41 of the cap element as described above, whereby the peripheral screw-like rotation of the protruding portion 51 of the adjusting element 5 is allowed within the recess portion 41 while undue removal of the adjusting element 5 from the cap element 3 is prevented.

At least one of the peripheral flap portion 21 of the adjusting element 5 comprises another protruding portion 53 as a thread portion on its inside. The thread portion 53 is so constructed that it is engaged with the thread portion 17 of the cap element 3 through the screw engagement mechanism, and thus the protruding portion 53 is present as a thread which is placed into the thread groove 47 of the thread portion 17.

A length along a spiral direction (i.e. the direction of the arrow B in FIG. 2) of the thread portion 53 is not specifically limited, and it may be very short. However, a length along a screw proceeding direction (i.e. the direction of the arrow C in FIG. 2) of the thread portion 53 is preferably such that the thread portion 53 is substantially tightly fitted into the thread groove 47 to achieve the screw like rotation, whereby rattling is prevented between the cap element 3 and the adjusting element 5, which improves adjustment accuracy of the pricking depth. The engagement of the thread groove 47 with the thread portion 53 makes the adjusting element 5 possible to go forward or backward relative to the cap element 3 along axis of these element when the adjusting element 5 is rotated relative to the cap element 3.

As seen from the drawings, the above rotation is limited by the stop portion 43 of the cap element 3. That is, the peripheral movement of the protruding portion 51 within the recess portion 41 is stopped by abutment of the protruding element 51 against the stop portion 43. In a preferable embodiment, upon being stopped, the protruding portion 51 abuts against the wall portion 61 or 63 at an edge on a lancet ejection side or an opposite side thereto of the recess portion 41. In this sense, the wall portions of the recess portion 41 function as stop means (one of the wall portions 63 simultaneously forms the stop portion 37). Thus, the protruding portion 51 moves along a combined direction of the directions of the arrows B and C (or opposite directions thereto), namely the direction of the thread upon the rotation of the adjusting element 5.

As described above, the cap element 3 comprises the recess portions 39 for clicking on the step portion 37 in the shown embodiment. The protruding portion 57 for clicking provided on the inside of the tab portion 23 of the adjusting element is fitted into the recess portions 39. In a clicking situation upon fitting as described above, when the cover element 7 is incorporated onto the adjusting element 5, there is a small space between the tab portion 23 and an inner wall of the cover element 7 as seen from FIG. 2. Thus, in a non-clicking situation, the adjusting element 5 moves between the cap element 3 and the cover element 7 while the tab portion 23 is opened outward a little. Such clicking and the movement as described are possible since the element constituting material can be deformed elastically.

When no clicking feeling is necessary, the recess portions 39 and the protruding portion 57 may be eliminated.

The adjusting element 5 has the recess portion 29 on its outside, which is so constructed that the protruding portion 65 (schematically shown in the broken line) provided on the inside of the cover element 7 is engaged with the recess portion 29. In a preferred embodiment, this engagement is easily formed by pushing the cover element 7 along the direction opposite to the arrow A onto the adjusting element 5, and easily disengaged by pulling the cover element 7 along the direction of the arrow A in a completed assembly. For example, the engagement and the disengagement are achieved by the use of interference fit. For the purposed of this, the recess portion 29 is preferably fully opened at the end surface of the adjusting element 5. The engagement state allows the adjusting element 5 and the cover element 7 to peripherally rotate together while the formation or the release of the engagement is possible by applying a force along the arrow A direction or the opposite direction thereto.

The cover element 7 comprises the opening 31 into which the adjusting element is inserted and the end surface 35 having the opening 33 against which the object to be pricked is placed. As shown in the drawings, the end surface 35 may be retracted a little from the end of the cover element 7.

When assembled as shown in FIG. 2, the adjusting element 5 is rotated upon the rotation of the cover element 7 around its axis, whereby the adjusting element 5 and the cover element 7 which is integral therewith moves forward or backward relative to the cap element 3 by means of the screw mechanism. That is, a length between the end surface 13 of the cap element 3 and the end surface 35 of the cover element 7 is changed, which enables the pricking depth of the pricking element to be adjusted.

In other words, the pricking depth corresponds to a protruding length of the pricking element from the end surface 35; since the movement of the lancet is stopped by the end surface 13 after the ejection of the lancet, when the length is changed between the end surfaces 13 and 35, the protruding length of the pricking element from the end surface (and thus the pricking depth) is changed even though the protruding length from the end surface 13 of the pricking element is constant. As easily seen from FIG. 2, the cover element 7 and the adjusting element 5 moves together relative to the cap element along the lancet ejection direction, whereby the distance between the end surfaces 13 and 35 is changed. The lancet is stopped by the stop means 13, and thus the protruding length of the pricking element from the end surface 35 is changeable.

In a preferred embodiment, the adjusting element 5 comprises at least one protruding portion 25 on its outside surface. The protruding portion 25 may be engaged with the recess portion 55 provided on the inside of the cover element 7 by means of snap-fitting. The numbers of the protruding portions 25 and the recess portions 55 are not specifically limited provided that sufficient engagement is achieved between the cover element 7 and the peripheral flap portions 21 of the adjusting element 5. This engagement prevents undue outward opening of the flap portions 21 of the adjusting element 5.

With resect to the present assembly, first the adjusting element 5 is put onto the end portion 11 having the end surface 13, and then the adjusting element 5 and the cap element 3 are then relatively rotated along the screw fastening directions so as to place the tab portions 23 on the step portions 37. When the rotation is continued thereafter, the tab portions 23 abut stop portions 43 so that the rotation is stopped.

When a slightly large force is applied in the above situation, leading ends of the tab portions 23 ride up the stop portions 43, which allows further rotation. This is because the provision of the slits 19 with the adjusting element 5 gives the elasticity to the adjusting element as a whole so that the peripheral flap portions 21 can be opened outward around the annular ring portion 45 as an axis (or as the base) with a small force. After riding over the stop portion, the adjusting element 5 returns to its original configuration due to its elasticity, and may be further rotated, whereby the adjusting element 5 further goes over the end portions 11. When the rotation is further continued thereafter, the protruding portions 51 provided on the inside of the tab portions are positioned inside the recess portions 41, so that further rotation is prevented. Thus, incorporation of the adjusting element 5 onto the cap element 3 is completed in this situation.

Then, the cover element 7 is incorporated onto the adjusting element 5 which has been incorporated onto the cap element 3. This incorporation may be carried out by moving the cover element 7 along the direction opposite to the arrow A so as to put the cover element 7 on the adjusting element 5 and engage the protruding portion 65 provided on the inside of the cover element 7 with the recess portion 29 of the adjusting element 5. Such movement fits the protruding portions 25 of the adjusting element into the recess portions 55 of the cover element, whereby the ends of the peripheral flap portions 21 and the tabs 23 push the step portions 37 properly. The term "properly" means that the cover element 7 and the adjusting element 5 incorporated together can be rotated relative to the cap element 3 with clicking at a predetermined interval by means of a force applied with fingers.

Incorporation of the cover element 7 as described above completes the assembly of adjusting the pricking depth of the present invention. The assembly thus completed is combined with an injector so that they are used for the blood collection.

Figure 3:
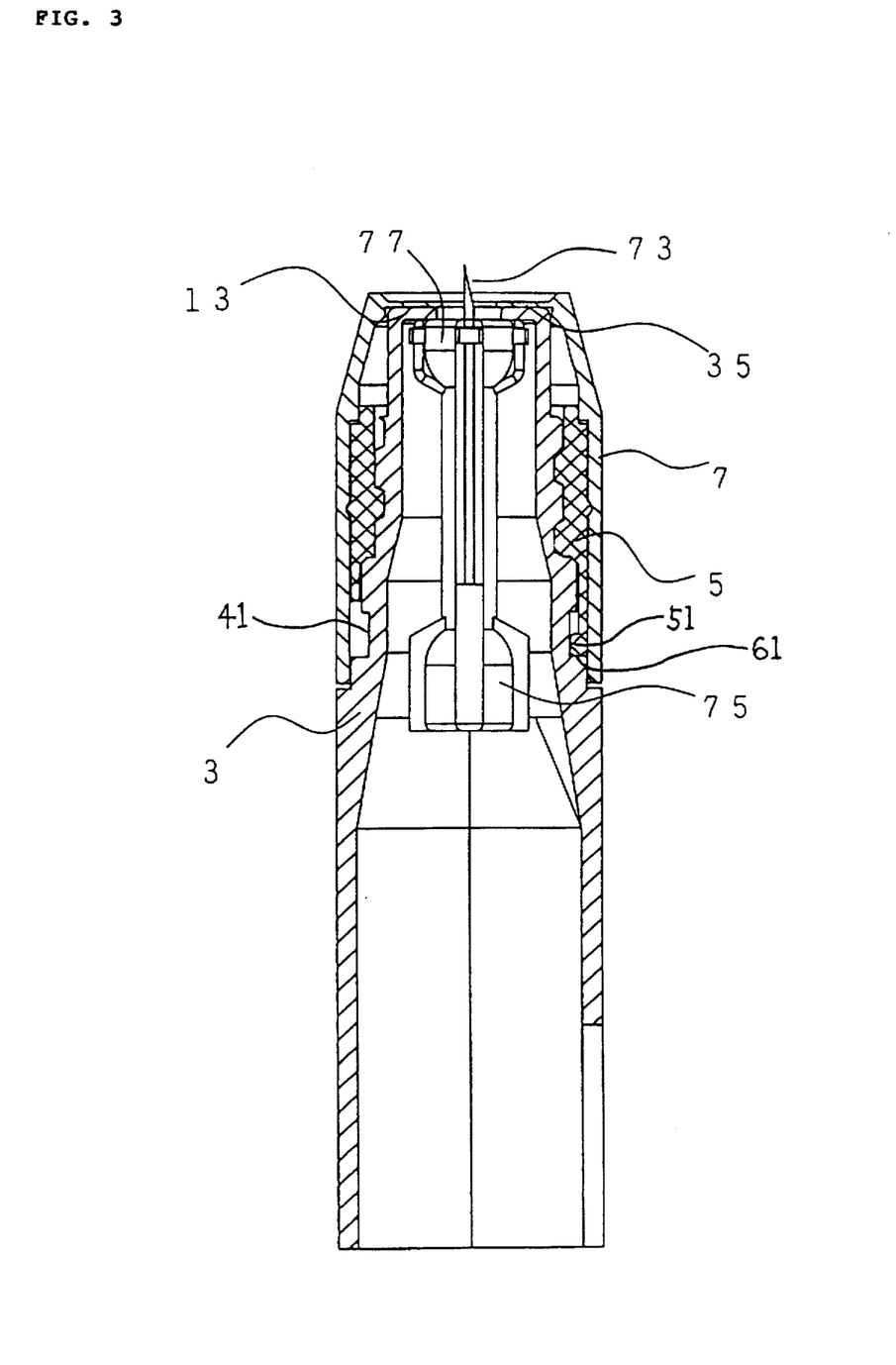
FIG. 3 schematically shows a cross sectional view of the assembly of adjusting the pricking depth of the pricking element according to the present invention which is set in a position of the longest pricking depth.
Figure 4:
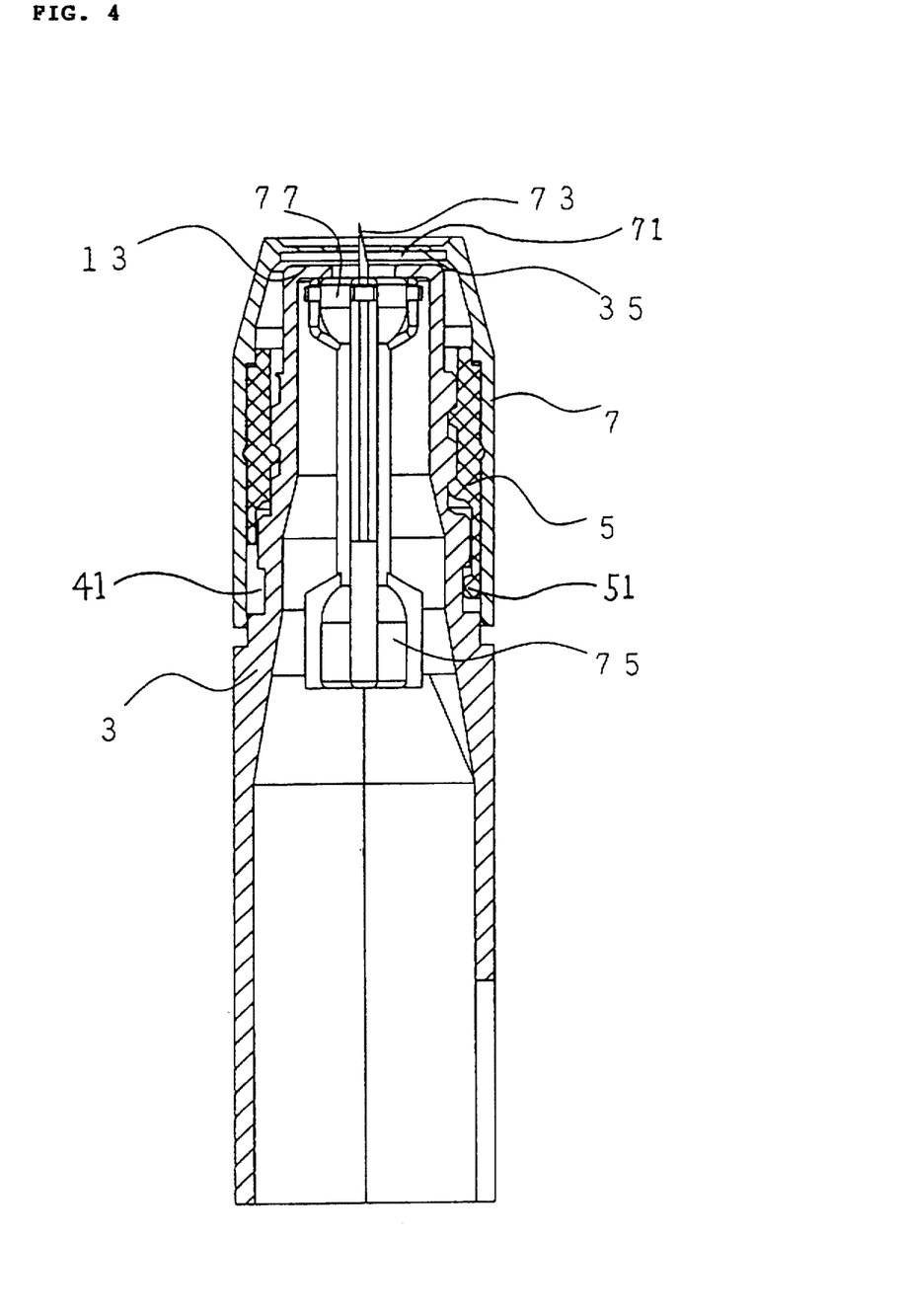
FIG. 4 schematically shows a cross sectional view of the assembly of adjusting the pricking depth of the pricking element according to the present invention which is set in a position of the shortest pricking depth.

The present assembly is based on the screw mechanism as described above. The assembly in a position of the maximum pricking depth is shown in FIG. 3 and the assembly in a position of the minimum pricking depth is shown in FIG. 4, each of which is shown in a schematic cross sectional view. As seen from the drawings, when the pricking depth is the maximum, the end surface 13 of the cap element 3 is in contact with the end surface 35 of the cover element 7, and when the depth is the minimum, there is a cavity 71 between these end surfaces. In addition, it is seen that the protruding portion 51 provided on the tab portion of the adjusting element 5 has moved within the recess portion 41 along the lancet ejection direction. In the embodiment shown in FIG. 3, the protruding portion 51 abuts against the wall portion 61.

FIGS. 3 and 4 show the lancet 75 having the protruding pricking element 73 at a moment when the end 77 of the lancet 75 has just abutted against the end surface 13 as the stop means. Thus, the protruding length of the pricking element from the end surface 35 is substantially equal to the pricking depth.

EXAMPLES

As the injector to which the present assembly is attached, "PENLET II" injector was selected which is commercially available from Lifescan (San Francisco, U.S.A.). In place of a cap element exclusively adapted to this injector, the present assembly was applied.

Figure 5:
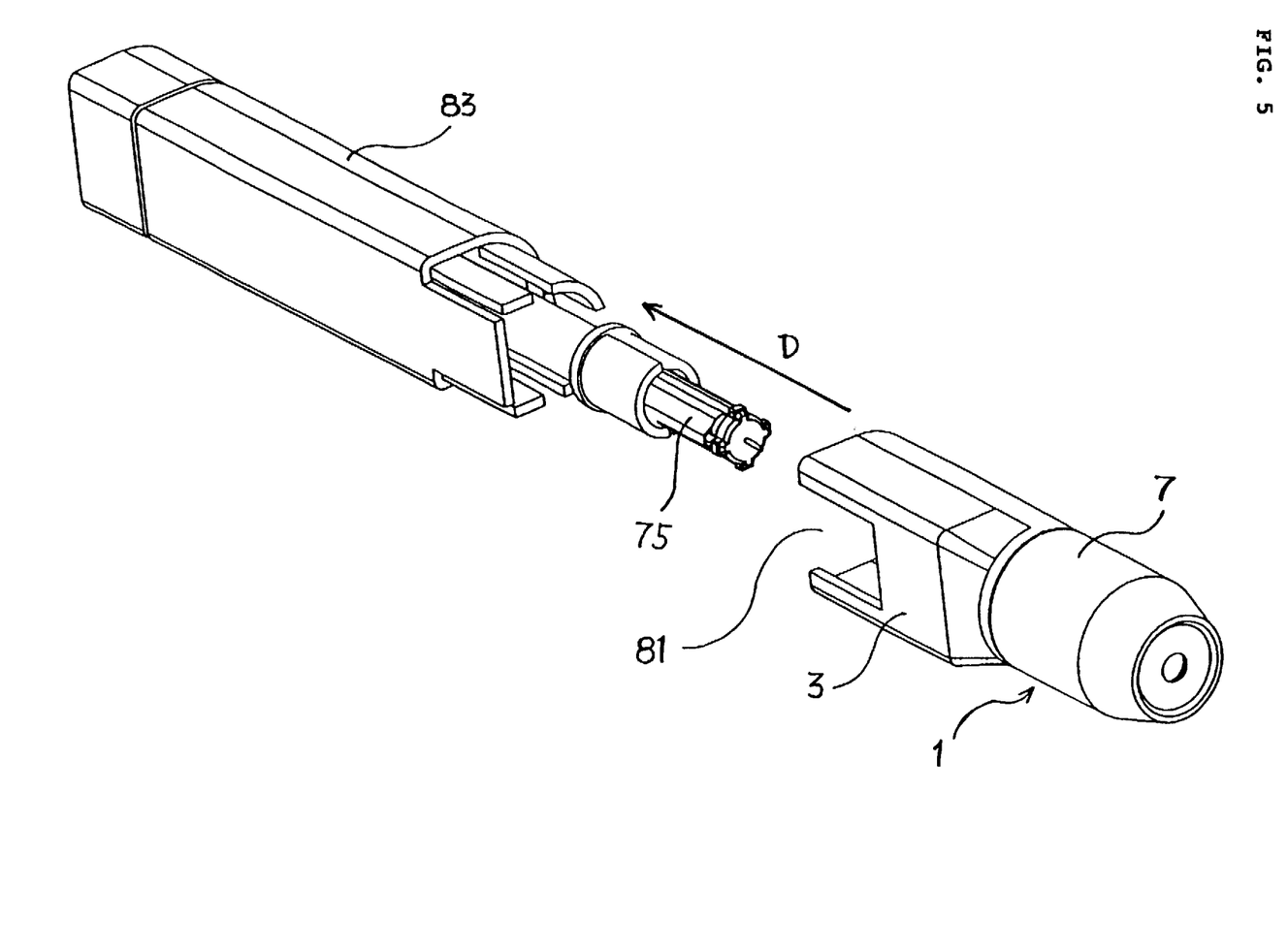
FIG. 5 schematically shows an exploded perspective view in which a manner to incorporate the assembly of the present invention into an injector is shown.

As shown in FIG. 5 in the exploded view, the rear end 81 of the cap element was provided with a cross section and an engagement means which allow the attachment of the cap element to the injector body 83 of "PENLET II" injector (thus, the same cross section and the same engagement means as those of the cap element of "PENLET II" injector), whereby the present assembly 1 including the cap element 3 was attached to the injector 83 so as to give it the pricking depth (multistage) adjusting function.

In FIG. 5, the injector 83 and the present assembly 1 are shown separately, but the attachment of the assembly to the injector is achieved by pushing, along the arrow D direction, the present assembly onto the injector 83 to which the lancet 75 has been attached.

Each element of the present assembly were formed using an injection molders and metal molds.

1) An ABS resin (Toyorac #500 commercially available from Toray Industries, Inc.) was used as a material for the cap element. The metal mold was fabricated for a single piece.

The thread portion, the stop portions and the recess portions and so on were formed in the end portions of the cap element, and only this end portion was fabricated into a split mold. As the molder, 40-ton injection molder (from Nissei Plastic Industrial Co., Ltd.) was used, and the molded elements were obtained. The cap element had the following sizes:

Total length 52.9 mm Width 14.6 mm Height 14.6 mm

Thickness of end surface as stop means 0.4 mm

The pitch of the thread was 4 mm, a rotation angle range of the adjusting ring was 90 degrees, and a difference between positions of the maximum pricking depth and the minimum pricking depth (thus, the pricking depth variable range) was 1.0 mm, which was divided into 5 stages by provisions of five recess portions for clicking. Thus, an adjustable pricking depth by a single stage was 0.25 mm each.

2) A polyacetal resin (Tenac #4520 commercially available from Asahi Chemical Industry Co., Ltd.) was used as a material for the adjusting element considering elastic properties, resistance to fatigue from flexing and sliding friction resistance with respect to the ABS resin.

The element was such that it had the protruding portions which fall into and connect to the recess portions of the cap element, the protruding portions which corresponds to the thread portions of the cap element, the four slits to divide the cylindrical wall into the flap portions, the recess portion which is engaged with the cover element and so on.

The metal mold was fabricated for a single piece. 20-Ton injection molder (Nissei Plastic Industrial Co., Ltd.) was used, and the molded elements having the following sizes were obtained:

Outer diameter 13.0 mm Inner diameter 10.04 mm Length 14.2 mm

When molded, mold release was smooth because of the four slits provided on the side surface, and the no sag at in the undercut portions or no deformation as the molded element was observed.

3) A PBT resin (PBT #1401X07 commercially available from Toray Industries, Inc.) was used as a material for the cover element considering resistance against body fluid contamination, texture upon handling, stiffness required to press the adjusting element against the cap element and so on.

Protruding portion was provided on the inside of the cover element.

The metal mold was fabricated for a single piece. 40-Ton injection molder (Nissei Plastic Industrial Co., Ltd.) was used, and the molded elements having the following sizes were obtained:

Length 22.0 mm Outer diameter 14.8 mm Inner diameter 13.3 mm

Thickness of end surface at front end 0.4 mm

4) Assembling

The adjusting element was pushed straight onto the cap element while both axes were aligned. Whenever the protruding portions provided on the inside of the tab portions of the adjusting element rode over the ridges of the thread portion provided on the cap element, the flap portions opened outward because of the elasticity of the adjusting ring (or element), in particular the elastic behavior of the flap portions, so that incorporation was easy even with straight pushing without rotation of the adjusting element. That is, the protruding portions provided on the inside of the tab portions were placed into the recess portions of the cap element.

The following was found: Even when the adjusting element was pushed onto in error (namely, when the end of the adjusting element abuts against the stop portion), the end of the adjusting element fell into the recess portion after riding over the stop portions of the cap element upon by rotating the adjusting element clock-wise or counterclock-wise.

Also, the following was found: When the adjusting element was rotated following the thread portion provided on the cap element, the end of the adjusting element abuts against the stop portion. However, the flap portions opened outward a little because of their spring properties, so that they rode over the stop portion on the cap element and finally fell into the recess portion properly.

When the cover element was put on the adjusting element incorporated onto the cap element, the ends of the adjusting element could not ride over the stop portions since outward opening of the flap portions was limited.

5) Function

The completed assembly of adjusting the pricking depth was attached to the injector without any problem.

Holding the cover element with fingers, the unitary cover element+adjusting element as the pricking depth adjusting mechanism was rotated to the first adjusting stage. The adjusting mechanism was stopped at a position of the first stage with a clicking sound.

When measured using a slide gauge, the cover element advanced 0.25 mm relative to the cap element. Then, rotating through the second stage to the fifth stage, and the rotation was surely stopped at every stage with the clicking sound and the advance length of 0.25 mm each. When reversely rotated, receding by every 0.25 mm was ensured.

The cover element did not slip on the adjusting element.

Holding the cover element, the assembly was detached from the injector ten times, and no problem was observed. The cover element was not likely to be pulled out of the adjusting element at all.

A lancet was attached to the injector, and then the present assembly was attached to the injector after setting to a predetermined pricking depth. Then, the lancet was ejected twenty times successively, and the adjusting mechanism was not changed from the set position at all.

Holding the cover element, the adjusting mechanism was set at from the first stage to the fifth stage, and then from the fifth stage to the first stage successively fifty times, after which whether or not the adjusting mechanism stopped at every stage correctly was checked. The mechanism surely stopped at the same positions as in the original assembly before testing.

Then, the assembly was disassembled and the presence of abrasion was checked with respect to the sliding portion between the cap element and the adjusting element. No abrasion sign was observed on the both elements.

Thereafter, re-assembling was carried out as described above, and no difference in the ease of assembling from the first assembling was observed in re-assembling and no problem was observed. The function of the assembly after re-assembling was not different at all.

Judging from the above examples, it is contemplated that the present assembly is suitable for the mass production in which no problem occurs in its function, and the assembly has stable product performance and quality.

We claim:

1. An assembly which is attached to an ejector which ejects a lancet having a pricking element protruding therefrom along an ejection axis, said assembly adjusting a pricking depth of the pricking element into an object to be pricked, the assembly comprising:

a cap member adapted for attachment to the ejector, the cap member having a stop means which stops movement of the lancet during ejection by abutment of an end of the lancet from which the pricking element protrudes against the stop means, a cover element having an opening against which the object to be pricked is placed, the pricking element extending through the opening when the lancet is ejected, and an adjusting element disposed between and engaging the cap element and the cover element, and a distance between the stop means and the opening along the ejection axis is changeable by rotation of the adjusting element around the ejection axis.

2. The assembly according to claim 1 wherein the cover element and the adjusting element are coupled together to rotate as a single structure about the ejection axis, and the adjusting element and the cap element are threadably engaged.

3. The assembly according to claim 2 wherein the cap element includes a cap element thread portion on an outer surface of an end portion of the cap element, the cover element includes a protruding portion on an inner surface thereof, and the adjusting element has an adjusting element thread portion on an inner surface thereof and a recess portion on an outer surface thereof, the adjusting element thread portion engaging the cap element thread portion and the recess portion of the adjusting element engaging the protruding portion of the cover element.

4. The assembly according to claim 2 wherein the adjusting element has a plurality of slits which extend from its end to be attached to the injector to divide the adjusting element into flap portions which are connected together at the opposite end of the adjusting element, the flap portions being elastically deformable.

5. The assembly according to claim 3 wherein the adjusting element further comprises a protruding portion and the cap element has a stop portion against which the protruding portion of the adjusting element abuts to limit rotation of the adjusting element.

6. The assembly according to claim 5 wherein the cover element limits elastic deformation of the adjusting element.

7. The assembly according to claim 2 wherein the adjusting element further comprises a protruding portion and the cap element has a stop portion against which the protruding portion of the adjusting element abuts to limit rotation of the adjusting element.

8. The assembly according to claim 7 wherein the cover element limits elastic deformation of the adjusting element.

9. The assembly according to claim 1 wherein the cap element includes a cap element thread portion on an outer surface of an end portion of the cap element, the cover element includes a protruding portion on an inner surface thereof, and the adjusting element has an adjusting element thread portion on an inner surface thereof and a recess portion on an outer surface thereof, the adjusting element thread portion engaging the cap element thread portion and the recess portion of the adjusting element engaging the protruding portion of the cover element.

10. The assembly according to claim 9 wherein the adjusting element has a plurality of slits which extend from its end to be attached to the injector to divide the adjusting element into flap portions which are connected together at the opposite end of the adjusting element, the flap portions being elastically deformable.

11. The assembly according to claim 10 wherein the adjusting element further comprises a protruding portion and the cap element has a stop portion against which the protruding portion of the adjusting element abuts to limit rotation of the adjusting element.

12. The assembly according to claim 9 wherein the adjusting element further comprises a protruding portion and the cap element has a stop portion against which the protruding portion of the adjusting element abuts to limit rotation of the adjusting element.

13. The assembly according to claim 12 wherein the cover element limits elastic deformation of the adjusting element.

14. The assembly according to claim 1 wherein the adjusting element has a plurality of slits which extend from its end to be attached to the injector to divide the adjusting element into flap portions which are connected together at the opposite end of the adjusting element, the flap portions being elastically deformable.

15. The assembly according to claim 14 wherein the adjusting element further comprises a protruding portion and the cap element has a stop portion against which the protruding portion of the adjusting element abuts to limit rotation of the adjusting element.

16. The assembly according to claim 15 wherein the cover element limits elastic deformation of the adjusting element.

17. The assembly according to claim 1 wherein the adjusting element further comprises a protruding portion and the cap element has a stop portion against which the protruding portion of the adjusting element abuts to limit rotation of the adjusting element.

18. The assembly according to claim 17 wherein the cover element limits elastic deformation of the adjusting element.

19. The assembly according to claim 1 wherein the cover element limits elastic deformation of the adjusting element.

20. A blood collection device for pricking an object comprising, in combination, a lancet having pricking member protruding therefrom, an ejector for ejecting the lancet, and an assembly for adjusting a pricking depth into the object to be pricked, said assembly being coupled to the ejector and comprising a cap element coupled to the ejector, the cap element having a stop means which stops movement of the lancet during ejection by abutment of an end of the lancet from which the pricking element protrudes against the stop means, a cover element having an opening against which the object to be pricked is placed, the pricking element extending through the opening when the lancet is ejected, and an adjusting element disposed between and engaging the cap element and the cover element, and a distance between the stop means and the opening along the ejection axis is changeable by rotation of the adjusting element around the ejection axis.

* * * * *